Figure 1:
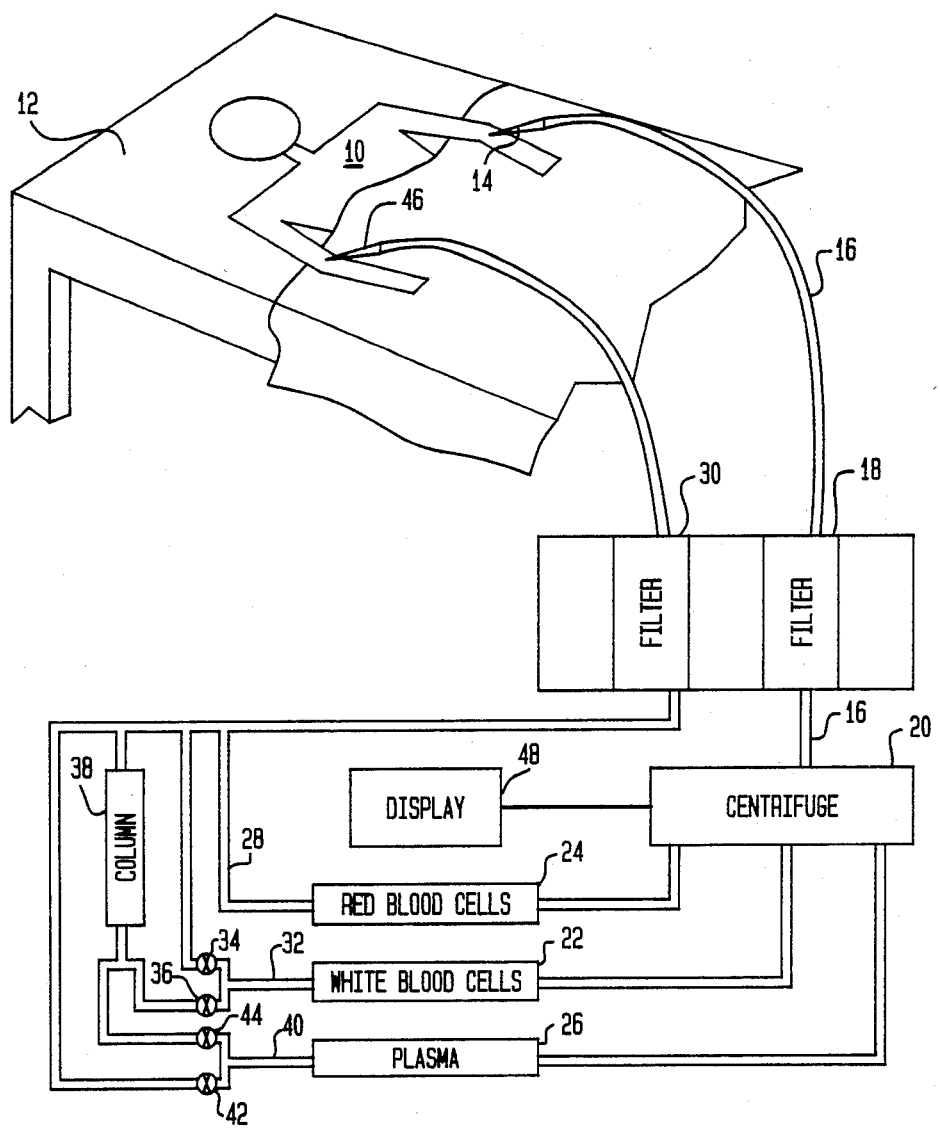

United States Patent [19]

Schneider

[11] Patent Number: 4,512,763
[45] Date of Patent: Apr. 23, 1985

[54] METHOD AND APPARATUS FOR SELECTIVE REMOVAL OF CONSTITUENTS OF BLOOD

[75] Inventor: Barbara Schneider, Philadelphia, Pa.

[73] Assignee: Gamma Medical Products, Inc., Glen Rock, N.J.

[21] Appl. No.: 259,971

[22] Filed: May 4, 1981

[51] Int. Cl.³ .............................................. A61M 1/03
[52] U.S. Cl. .............................................. 604/5; 604/6
[58] Field of Search ........... 128/214 R, 214 B, 214 G, 128/214.2, 233, 272, DIG. 3; 210/650, 651, 321.3; 424/85; 604/4–6, 19, 28–29, DIG. 3; 436/518, 528, 531–532

[56] References Cited

U.S. PATENT DOCUMENTS

| | | | |
|---|---|---|---|
| 3,655,123 | 4/1972 | Judson et al. | 604/6 |
| 3,857,393 | 12/1974 | Rose | 604/6 |
| 3,964,467 | 6/1976 | Rose | 424/85 |
| 4,111,199 | 9/1978 | Djerassi | 128/214 R |
| 4,170,056 | 10/1979 | Meyst et al. | 128/214 B |
| 4,215,688 | 8/1980 | Terman et al. | 604/5 |

Primary Examiner—Kyle L. Howell
Assistant Examiner—Francis J. Jaworski
Attorney, Agent, or Firm—R. Martin Oliveras

[57] ABSTRACT

A method for removing a constituent such as immunoglobulins, lymphocytes, or immune complexes from a component of a patient's blood comprises the steps of: removing blood from the patient; separating the constituent containing component from the rest of the patient's blood; preparing an antibody; contacting the constituent containing component with the antibody so that the antibody may adsorb the constituent from the component; recombining the antibody contacted constituent containing component with the other components of the removed blood; and injecting the combined components of blood into the patient; wherein the adsorbing antibody is prepared by the steps of: removing selected cells from the constituent containing component of the patient's blood; injecting the removed cells into a non-human animal; allowing the non-human animal to manufacture antibodies to the injected cells; removing blood from the non-human animal; separating the same constituent containing component from the removed blood of the non-human animal; and removing the antibody from the constituent containing component of the non-human animal's blood. Another method for making the adsorbent antibody includes the steps of: creating cell cultures; cloning the antibody producing cells; removing large quantities of the antibody; and purifying the antibody. General and specific apparatus for effecting the above methods are also disclosed.

18 Claims, 2 Drawing Figures

METHOD AND APPARATUS FOR SELECTIVE REMOVAL OF CONSTITUENTS OF BLOOD

BACKGROUND OF THE INVENTION

The purification of blood externally of a living patient is a medical practice used in the treatment of certain liver disorders, immune complex diseases, hematological disorders, neurologic diseases, transplant rejection and malignancies. For example, it is a practice today in the treatment of the above diseases to withdraw blood from one arm of a patient, to feed the blood into a processor which separates the red blood cells from other constituents of the blood by means of a centrifuge, and to return the red blood cells to the patient via his other arm. An example of the apparatus conventional in such an operation is the IBM Model 2997 Cell Processor. Other examples are the Fenwal CS 3000 System manufactured by Fenwal Laboratories, division of Travend Laboratories, of Deerfield, Ill., and the Haemonet ics, Model 30, manufactured by Heamonet ics Corporation of Braintree, Mass.

Filters commonly referred to as "cylinders" or "columns" have in the past been attached into the tubes of cell processors as described above for the purpose of performing an operation on the blood passing through the cylinder. These known prior devices customarily employ coated glass or plastic beads to assist in the removal of cells and/or plasma components through a process of adsorption. One such unit, by way of example, is the heparin-agarose column made by Dr. A. A. Pineda of the Mayo Clinic. Such columns, though relatively ineffective, have been utilized in an attempt to remove cholesterol from the blood.

In addition, experiments have been conducted on the ex vivo removal of lymphocytes in the laboratory. These laboratory experiments generally involve the problems of unsecured beads which cannot be returned to a human body because the probability of embolization with disastrous results to the patient would be unacceptably high. Another problem associated with the laboratory techniques is the processing time. For example, the rate of flow through the filter must be sufficient to keep the patient alive, i.e. the blood cannot be removed from a patient, processed, and then returned to him after any considerable delay.

Still another problem associated with the laboratory techniques is the low rate of efficiency of the antigen-antibody interaction.

A further problem involves damage to the blood as a result of the impact thereof upon a rigid cylinder or column in the processing operations. The known columns used in such laboratory experiments are made of glass and/or stainless steel.

Additional problems include non-specific absorption by column materials of cells or of plasma components of the blood which it is desirable to return to the patient.

It is accordingly an object of the present invention to obviate many of the problems described above and to provide a novel method and apparatus for the selective removal of blood constituents.

It is another object of the present invention to provide a novel method and apparatus for the selective removal of blood constituents such as lymphocytes, lymphocyte subsets, antigen-antibody complexes, immunoglobulins and immunoglobulin subclasses on a highly selective basis.

It is yet another object of the present invention to provide a novel method and apparatus for the selective removal of constituents of blood with a significantly decreased processing time.

Still a further object of the present invention is to provide a novel method and apparatus for the highly selective removal of constituents from blood which is significantly less damaging to the blood constituents returned to the patient.

It is still a further object of the present invention to provide a novel method and apparatus for the selective removal of blood constituents in which the probability of problems related to constituent materials is significantly reduced.

Still a further object of the present invention is to provide a novel fiber for use in the removal of blood constituents.

Yet a further object of the present invention is to provide a novel set of constituent antibody and antibody materials membrane fragments and receptors, useful for diagnosis and treatment of a wide variety of diseases and in the selective removal of blood constituents.

These and other objects and advantages will be readily apparent from the claims when considered in connection with the following detailed description and appended drawings.

THE DRAWINGS

Figure 2:
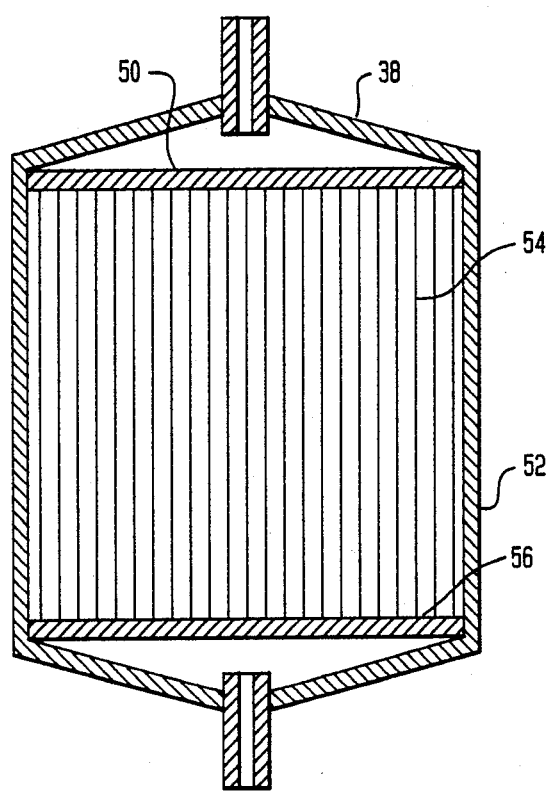

FIG. 1 is a schematic representation of a patient receiving a treatment utilizing the apparatus of the present invention; and FIG. 2 is a pictorial representation in cross section of one embodiment of a filter of the present invention.

THE DETAILED DESCRIPTION OF PREFERRED EMBODIMENTS

With reference to FIG. 1, a patient 10 is shown in a supine position on a bed or other appropriate supporting structure 12 with a needle 14 placed in his arm for the removal of whole blood. The blood from the patient is conveyed by way of an appropriate tubing 16 through a filter 18 to a centrifuge 20 where the red blood cells are separated from the white blood cells and plasma in appropriate containers 22, 24 and 26 respectively. The red blood cells are conveyed by way of tubing 28 to a suitable and conventional bacterial filter 30. The white blood cells are taken by way of tubing 32 and valve 34 to the filter 30, or alternatively taken through the valve 36 to the novel filter or column 38 of the present invention for the selective removal of constituents of the blood. Similarly, the plasma may be applied through a tube 40 and a valve 42 to the filter 30, or alternatively through a valve 44 to the column 38. The filter 18 serves to remove fine clots or cellular debris on the inflow side, and the filter 30 serves to remove similar materials on the outflow side. The blood from the patient recombined in the filter 30 is fed by gravity into a vein of the patient through a conventional needle 46.

While not shown in FIG. 1, saline solutions may be used in a conventional manner to prime the system.

The system may also be provided with an appropriate conventional display 48, desirably of the digital readout type.

As illustrated in FIG. 1, the column may be selectively used to remove lymphocytes from the white blood cells or to remove immune complexes, immunoglobulins, cholesterol or other constituents from the plasma.

The cell processor as described above in use with the filter of the present invention may be of any suitable conventional type and, by way of example, may be a Fenwal CS 3000 System obtainable from the Fenwal Corporation of Deerfield, Ill., or Haemonetics Model 30 obtainable from Haemonetics Corporation of Braintree, Mass.

As a practical matter, the rate of blood flow must be between about 30 ccs. to 60 ccs. per minute because of the possible adverse effects upon the rate of component removal. This is particularly true when dealing with children who have a small blood volume of blood.

With respect to FIG. 2 where a first embodiment of the column 38 of FIG. 1 is illustrated, the inlet tube may be attached by any suitable conventional means to the generally cylindrical top or spreader 50 made of glass, plastic or stainless steel. The spreader 50 supports the column by means of suitable inert supports. The exterior 52 of the column may be rigid and made of glass, plastic or metal. Alternatively, it may be a bag of relatively flexible nylon or other plastic.

Within the bag 52, the spreader 50 may take the form of a cylindrical plate made of plastic. This plate may be provided with a plurality of apertures to which one end of a fiber may be secured. The method of securing the fibers 54 may be by any conventional means, e.g. by weaving or welding.

Also suspended within the bag 52 is a second cylindrical plate 56 which may conform in every material respect to the plate 50 described above. Each pair of plates 50, 56 form an active filter section, and the column may include a number of such active filter sections.

In addition to the apertures through which the fibers 54 are secured, the plate 50 may be provided with a number of apertures through which blood entering the container 38 may flow under the influence of gravity.

Other methods of securing the fibers to the plates may be used where the structure insures the flow of the blood over the surface of the antibody coated surfaces of the filter. For example, the antibody coated fibers 54 may be suspended in an aperture in the plate 50 in a manner such that blood plasma will flow through the column only down the filters 54 because of the natural surface tension of the blood plasma and the contact thereof with the fiber at the plate 50.

In lieu of the plates, the fibers may be directly attached to the upper and lower borders of the column or bag on which they are contained. They may also be arranged in a spiral rather than parallel fashion to increase the amount of adsorption area without increasing the overall dimensions of the column or bag.

The ratio of the diameter of the column to the length of the filters is important. Those dimensions are desirably about 5 cm. in diameter and about 12.5 cm. in length for a ratio of about 2.5. In the example described above, the ratio of the holes in the plates to the number of fibers is important and is desirably about one hole for each ten fibers.

The length and surface area of the fibers is a function of the blood constituent desired to be removed. The cross-sectional area of the fiber is desirably between about 0.05 mm. and 0.25 mm. and the length of the fiber is between about 11.5 cm. and about 12.5 cm.

The ratio of the length of the tubes to the volume of fluid passing through the column per unit of time is desirably between about 11.5 cm. and about 12.5 cm.

The fibers 54 may be provided with a coating of about 0.05 microns in thickness, although the thickness of the coating may depend upon the blood constituent desired to be removed. It is important that the surface area of the fiber be rough, as in partially digested nylon fibers, to maximize the surface area thereof. For example, a fiber consisting of carbon may be used with a coating of Monoclonal antibodies OKT3PAN, OKT-4IND, OKT6THY, OKT8SUP available from the ORTHO Corporation of Raritan, N.J. These are monoclonal antibodies to specific lymphocyte subtypes and are adapted for the selective removal of these cells from the blood.

In lieu of the fibers illustrated in FIG. 2, the antibody material carrying substance may be in the form of sheets or strips down which the blood will flow in much the same manner as the trickler plates of a cooling tower.

Numerous matrices including colloidion coated charcoal, agarose, agar, polyacrylamide gelatin, sepharose, sephadex, glass, methacrylate and nylon have been employed as immuno or general affinity adsorbents. For removal of lymphocytes from whole blood, the use of nylon with human immunoglobulins covalently bound to it as the matrix tend to reduce or eliminate problems such as poor flow, high cost, danger of cell rupture, and the presence of potential carcinogens which may mitigate against use of one or more of the other matrices.

Strips of nylon stocking material may be used. In this process, the stocking material may be cut into strips and subjected to the following:

(a) soak strips in petroleum ether and wash with agitation for ten (10) minutes;
(b) repeat step (a) using 3 washes of 95% ethanol, about two (2) minutes each;
(c) wash with three (3) washes 0.1 molar HCl, about two (2) minutes each;
(d) separate the nylon into two (2) batches;
(e) saok one (1) batch in 3-N HCl for about 30 minutes at about 37° C., soak the other batch in 3-N HCl for about 30 minutes at about 22° C. to partially degrade the nylon;
(f) wash the nylon copiously with distilled or deionized water until the pH of the effluent is pH 5-6 to stop the degradation process;
(g) combine one-half of one batch with one-half of the other batch to create two (2) new batches;
(h) treat one new batch with a 5 mg/ml solution of 1 ethyl 3-(3-dimethylaminopropyl)carbodiimide hydrochloride (EDC) in 20 ml of 0.15 molar NaCl in NaAc/HAc pH 5.5, 0.05 molar 30 seconds vigorously to provide a coupler;
(i) treat the other new batch with 1 cyclohexyl 3-(2-morpholinethyl)-carbodiimide metho-p-toluene sulfonate (CMC) instead of EDC as described in step (h);
(j) add 10 ml of the same buffer containing purified human gammaglobulins or Cohn fraction 11, stirring gently and let stand 30 minutes;
(k) wash with 5 liters of PBS; and
(l) refrigerate until used.

The process as described about produces four different preparations for use in eliminating lymphocytes. Rheumatoid factor may be attached to the nylon matrix in a similar fashion.

EXAMPLES

The operation of the present invention may be understood with specific reference to the following examples which are to be taken as illustrative and not limiting:

EXAMPLE 1

A patient suffering from immune complex was treated by the conventional removal of whole blood and the conventional separation thereof into (a) red blood cells (b) plasma, and (c) white blood cells. The plasma contains the entire immunological history of the patient including about three hundred proteins and rheumatoid factors. The plasma was passed through a filter of the present invention of 6.0 cm. in circumference and containing 60 sheets of nylon of 0.05 mm. cross-section and 12.5 cm. length. The sheets of fiber provided a ratio of active surface area to cylinder size/blood rate of flow of 35–45 ml/min. Each of the fiber sheets were treated to establish the covalent binding of immunoglobulin or other reactant (rheumatoid factor or Fc receptor) to a partially degraded nylon filter material.

The blood passing through the filter was sampled 15 minutes after the process began and analysis has shown 80% reduction in lymphocyte population, i.e. the removal of 80% of the lymphocyte entering the cylinder with the blood. This result is consistent with the reduction in immunoglobulins obtained with other constituents.

Antibody Preparations

One of the adsorbents that can be used in cases similar to Example 1 can be prepared by the steps of:

To prepare antibody to (HLA-DRw):

(a) obtain purified T cells from EBV negative and EBV positive adult and pediatric donors by any suitable conventional technique;

(b) add the purified T cells to cultures of EBV infected cells;

(c) test transformed T cells from these cultures for the presence of HLA-DR;

(d) inject a purified aliquot of the T cells (or a membrance fraction) into a suitable non-human animal such as a goat, rabbit, or the like;

(e) test the injected animal at an appropriate time for production of an antibody to HLA-DR;

(f) adsorb out all other T cell directed antibodies by using lymphocytes devoid of HLA-DR; and (f) harvest the antibody for reagent purposes.

EXAMPLE 2

Removal of immunoglobulin or immune complexes by using rheumatoid factor as the adsorbent.

The antibody prepared for use in Example 2 was prepared by the steps of:

(a) drawing blood from the veins of adult or pediatric patients with rheumatoid arthritis and high titers (e.g. 1:500 or greater) of rheumatoid factor;

(b) subjecting the blood to fractionation and harvesting a layer of purified B lymphocytes in any suitable conventional manner;

(c) rosetting out those B lymphocytes positive for rheumatoid factor;

(d) placing the purified B lymphocytes containing less than 3% thymphocytes and phagocytic cells into sterile culture;

(e) If B cells do not grow unaided, superinfecting these cells with EBV strain B95-8;

(f) testing culture for the presence of rheumatoid factor by two methods such as latex fixation, hemagglutinin;

(g) separating and diluting cells from cultures exhibiting appropriate levels of rheumatoid factor until a single cell of culture is reached in an attempt to produce monoclonal antibodies;

(h) separating the monoclonal antibodies; and (i) expanding the cultures of such cells and isolating by any suitable conventional method the rheumatoid factor for reagent purposes.

EXAMPLE 3

Removal of immunoglobulin or immune complexes by using purified Fc receptor as the immuno-adsorbent.

The antibody prepared for use in Example 3 was prepared by the steps of:

(a) obtaining a purified culture of a Fc receptor containing cell line, e.g. K562 or NK cells superinfected with EBV B95-8 if they will not grow unaided;

(b) allowing the cells to grow in culture and harvesting the supernatant, or alternatively growing the cells in culture and then heating to about 40° C. to increase the rate of removal of Fc receptor, then cooling the cells and removing the supernatant; and (c) purifying the Fc receptor fraction for use in humans by standard immunologic technique.

The principles, preferred embodiments and modes of operation of the present invention have been described in the foregoing specification. The invention which is intended to be protected is not, however, to be constructed as limited to the particular forms disclosed, since these are to be regarded as illustrative rather than restrictive. Variations and changes therefore may be made by those skilled in the art without departing from the spirit and scope of the present invention.

What is claimed is:

1. A method of removing a constituent such as immunoglobulins, lymphocytes, or immune complexes from a component of a patient's blood comprising the steps of:

(a) removing a volume of the patient's blood from a vein;

(b) separating the constituent containing component from the removed blood;

(c) preparing an antibody;

(d) contacting the patient's component with the antibody so that the antibody may adsorb the appropriate constituent from the component;

(e) recombining the antibody contacted component with the other components of the patient's blood; and (f) injecting the combined components into a vein of the patient; wherein the antibody is prepared by the steps of:

(g) removing a volume of the patient's blood;

(h) separating the component from the removed blood;

(i) removing selected cells from the component;

(j) injecting the removed cells into a non-human animal such as a goat, rabbit or mouse;

(k) delaying sufficient time for the non-human animal to manufacture antibodies to the injected cells;

(l) removing blood from the non-human animal;

(m) separating the same component from the removed non-human animal's blood; and (n) removing the antibodies from the non-human animal's component.

2. A method of removing a constituent such as immunoglobulins, lymphocytes, or immune complexes from a component of a patient's blood comprising the steps of:
(a) removing a volume of the patient's blood from a vein;
(b) separating the constituent containing component from the removed blood;
(c) preparing an antibody;
(d) contacting the patient's component with the antibody so that the antibody may adsorb the appropriate constituent from the component;
(e) recombining the antibody contacted component with the other components of the patient's blood; and
(f) injecting the combined components into a vein of the patient; wherein the antibody is made by the stpes of:
(g) removing a volume of the patient's blood;
(h) separating the component from the removed blood;
(i) removing selected cells from the component;
(j) creating cultures of these cells grown in nutrient media and testing these cells for the presence of the antibody;
(k) cloning the created cells;
(l) heating of cells to remove large quantities of portions of the antibody; and
(m) purifying the portion of the antibody.

3. Apparatus for removing a constituent such as immunoglobulins, lymphocytes, or immune complexes from a component of a patient's blood comprising:
means for removing a volume of the patient's blood from a vein;
means for separating the constituent containing component from the removed blood;
means for contacting the patient's component with an antibody capable of adsorbing said constituent from the component, wherein said antibody is fixed relative to said contacting means;
means for recombining the antibody contacted component with the other components of the patient's blood; and
means for injecting thhe re-combined components into a vein of the patient.

4. The apparatus of claim 3 wherein said contacting means includes:
a matrix; and
means for spreading the blood component in a generally horizontal direction to contact said matrix at the upper end thereof, whereby the blood component will flow downwardly in contact with said matrix to the lower end thereof; and means for collecting the blood component from the lower end of said matrix.

5. The apparatus of claim 4 wherein said contacting means includes partially digested nylon.

6. The apparatus of claim 3 wherein said blood volume removing means operates at a rate of from 30 to 60 cc/minute.

7. Apparatus for removing a constituent such as immunoglobulins, lymphocytes, or immune complexes from a component of a patient's blood comprising:
means for removing a volume of the patient's blood from a vein;
means for separating the constituent containing component from the removed blood;
means for contacting the patient's component with an antibody capable of adsorbing said constituent from the component;
means for recombining the antibody contacted component with the other components of the patient's blood; and
means for injecting the re-combined components into a vein of the patient; wherein said component contacting means further comprises:
an input plate structure for receiving the constituent containing component from the separating means and including a plurality of appertures;
an output plate structure for providing the antibody contacted component to said recombining means and also including a similar plurality of apertures; and
a plurality of fibers for interconnecting corresponding appertures located on said input and output plate structures and including said constituent adsorbing antibody covalently bound thereto.

8. The apparatus of claim 7 wherein said fibers are in parallel arrangement.

9. The apparatus of claim 7 wherein said constituent containing component remains in contact with said fibers due to the natural surface tension between the component and the fibers.

10. The apparatus of claim 7 wherein the received constituent containing component flows onto the ends of said fibers at the input plate structure under the influence of gravity.

11. The apparatus of claim 7 wherein the diameter of said input and output plate structures is approximately 5 cm and wherein the length of said fibers is approximately 12.5 cm.

12. The apparatus of claim 7 wherein each plate structure includes approximately one apperture for each ten fibers.

13. The apparatus of claim 7 wherein said fibers have a diameter of approximately 0.05 mm and a length of approximately 12.5 cm.

14. The apparatus of claim 7 wherein said adsorbent antibody on said fibers has a thickness of approximately 0.05 microns.

15. The apparatus of claim 7 wherein said constituent is a specific lymphocyte subset; said fibers are made of carbon; and said adsorbent antibody is a monoclonal antibody.

16. The apparatus of claim 7 wherein said fibers are made of nylon.

17. The apparatus of claim 7 wherein said constituent is a specific lymphocyte subset; said fibers are made of nylon; and said adsorbent antibody is a human immunoglobulin.

18. The apparatus of claim 7 wherein said plate structures have a diameter of approximately 5 cm; said fibers are made of partially digested nylon and have a diameter of approximately 0.05 mm and a length of approximately 12.5 cm; and wherein said adsorbent antibody is an immunoglobulin or other reactant such as rheumatoid factor or Fc receptor.

19. Apparatus for removing a constituent such as immunoglobulins, lymphocytes, or immune complexes from a component of a patient's blood comprising:
means for removing a volume of the patient's blood from a vein;
means for separating the constituent containing component from the removed blood;

means for contacting the patient's component with an antibody capable of adsorbing said constituent from the component;

means for recombining the antibody contacted component with the other components of the patient's blood; and means for injecting the re-combined components into a vein of the patient; wherein said contacting means further comprises strips or sheets of nylon.

* * * * *